United States Patent
Mollenauer et al.

(10) Patent No.: US 6,468,292 B1
(45) Date of Patent: Oct. 22, 2002

(54) SKIN SEAL WITH INFLATABLE MEMBRANE

(75) Inventors: Kenneth H. Mollenauer, Santa Clara; Michelle Y. Monfort, Los Gates, both of CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/383,027

(22) Filed: Aug. 25, 1999

Related U.S. Application Data

(63) Continuation of application No. 08/867,285, filed on Jun. 2, 1997, now Pat. No. 5,964,781, which is a continuation of application No. 08/444,425, filed on May 19, 1995, now Pat. No. 5,634,937.

(51) Int. Cl.[7] .............................................. A61B 17/08
(52) U.S. Cl. ........................ 606/213; 606/192; 604/256
(58) Field of Search ................................ 606/213, 192; 604/116, 167, 237, 115, 256, 264; 600/32

(56) References Cited

U.S. PATENT DOCUMENTS

| | | | |
|---|---|---|---|
| 1,690,995 A | 11/1928 | Pratt | |
| 3,402,710 A | * 9/1968 | Paleschuck | 604/264 |
| 3,797,478 A | * 3/1974 | Walsh et al. | 604/256 |
| 4,555,242 A | 11/1985 | Saudagar | 606/213 |
| 4,796,629 A | 1/1989 | Grayzel | 606/194 |
| 5,211,633 A | 5/1993 | Stouder, Jr. | 604/167 |
| 5,273,545 A | 12/1993 | Hunt et al. | 604/167 |
| 5,360,417 A | 11/1994 | Gravener et al. | 604/278 |
| 5,366,478 A | * 11/1994 | Brinkerhoff et al. | 604/256 |
| 5,391,156 A | 2/1995 | Hildwein et al. | 604/174 |
| 5,403,336 A | 4/1995 | Kieturakis et al. | 606/167 |
| 5,413,571 A | 5/1995 | Katsaros et al. | 606/213 |
| 5,460,616 A | 10/1995 | Weinstein et al. | 604/167 |
| 5,514,109 A | 5/1996 | Mollenauer et al. | 604/249 |
| 5,514,133 A | 5/1996 | Golub et al. | 606/1 |
| 5,545,179 A | 8/1996 | Williamson, IV | 606/213 |
| 5,607,443 A | 3/1997 | Kieturakis et al. | 606/192 |
| 5,634,937 A | * 6/1997 | Mollenauer et al. | 606/213 |
| 6,004,303 A | 12/1999 | Peterson | |
| 6,197,002 B1 | 3/2001 | Peterson | |

* cited by examiner

*Primary Examiner*—David O. Reip
*Assistant Examiner*—Julian W. Woo

(57) ABSTRACT

A skin seal or trocar stabilizer with an inflatable balloon in the shape of a dumbbell, where the balloon may be stored within a cannula for easy placement in an incision and inflated to deploy the balloon inside the body, and a portion of the balloon expands inside the cannula, whereby medical instruments may be passed through the skin seal into a laparoscopic workspace while the balloon is inflated, thereby allowing the use of normal short surgical instruments during laparoscopic procedures and during insufflation.

25 Claims, 8 Drawing Sheets

SKIN SEAL WITH INFLATABLE MEMBRANE

CROSS REFERENCE TO RELATED APPLICATIONS

The present application is a continuation of U.S. application Ser. No. 08/867,285, filed on Jun. 2, 1997, now U.S. Pat. No. 5,964,781, which is a continuation of U.S. application Ser. No. 08/444,425, filed on May 19, 1995, now U.S. Pat. No. 5,634,937. The priority of these prior applications is expressly claimed and their disclosures are hereby incorporated by reference in their entirety.

FIELD OF THE INVENTION

This invention relates to the field of surgical endoscopy, specifically to improvements in skin seals and cannulas.

BACKGROUND OF THE INVENTION

Surgical endoscopy is a surgical technique of using small diameter long-handled tools such as graspers, forceps, scissors, refractors, dissectors, and clamps specially designed to be inserted through small incisions in the skin (or other openings in the body) to perform operations within the body. The surgeon performing the surgery often cannot see the operation directly and must watch the procedure on a video monitor fed by an endoscopic camera or endoscope. Endoscopic surgery replaces open surgery that requires large incisions, essentially opening the body cavity completely, in order to perform surgery deep within the body. Endoscopic techniques have been used for gall stone removal, gall bladder removal, hernia repair, tumor removal, lymph node removal, appendectomy, and many other operations. Endoscopic surgery is also called laparoscopic surgery, video assisted surgery, minimally invasive surgery, and bandaid surgery, but throughout this specification the term endoscopic surgery or laparoscopic surgery will be used.

To illustrate the background of the inventions described below, the example of the laparoscopic cholecystectomy, hernia repair, or lymphadenectomy, as well as the operation for harvesting a blood vessel, will be used to illustrate both the old laparoscopic procedures and the new laparoscopic procedures now possible with the new devices. In the old procedure, a working space was created in the abdomen using the process called pneumoperitoneum or insufflation. Insufflation is the process of injecting gas into the body to blow it up like a balloon, creating a chamber filled with gas. When performed on the abdomen, the peritoneum is inflated and the procedure is known as pneumoperitoneum. The procedure can be used for inflating a space between the peritoneum and the skin to permit laparoscopic hernia repair, as illustrated in U.S. Pat. No. 5,496,345, issued to Kieturakis et al. and entitled "An Expansible Tunneling Apparatus for Creating an Anatomic Working Space." Insufflation can be used also to inflate a tunnel shaped working space over a blood vessel, to facilitate blood vessel harvesting, as described in U.S. patent application Ser. No. 08/267,484, entitled "Extraluminal Balloon Dissection Apparatus and Methods," incorporated herein by reference. While the chamber is filled with gas, the surgeon inserts long slender laparoscopic tools through trocars and cannulas that pierce the skin and provide access ports into the insufflated chamber.

For abdominal surgery, such as a cholecystectomy, (gall bladder removal), the insufflation is accomplished by the following procedure. An incision is made at the lower edge of the belly button or umbilicus. The surgeon uses his fingers or a blunt dissection tool, such as a blunt nosed obturator, to uncover the fascia or abdominal muscles, then a large needle, referred to as a Verres needle, is inserted into the abdomen or peritoneal cavity. The Verres needle punctures the fascia and peritoneum that cover the abdomen. A pressurized gas such as $CO_2$ is injected into the abdomen through the needle, in effect inflating the abdomen like a balloon. After the abdomen is inflated, the Verres needle is removed. After the needle is removed, trocars and cannulas are inserted into the space created by the insufflation. Endoscopic instruments, including an endoscope or laparoscope, scissors, graspers, etc., are inserted into the abdomen through the cannulas and manipulated to dissect tissue surrounding the gallbladder, remove the gall bladder, and stitch the internal wounds.

To harvest the saphenous vein using laparoscopic procedures, the surgeon may insufflate a tunnel shaped workspace over a blood vessel. The tunnel is first created using obturators, tunneling devices, or balloons inserted through small incisions along or over the saphenous vein. After the tunnel is created, the surgeon may insert skin seals and cannulas, and insufflation gas is injected through one of the trocars. While the tunnel is insufflated, the cannulas permit the surgeon to insert laparoscopic instruments into the tunnel to perform surgery on the saphenous vein.

The cannula used in the procedures described above is a length of rigid tube. The trocars and cannula are designed to allow laparoscopic instruments to pass through them and prevent gas from escaping the abdomen or other insufflated work space. The cannula may have a flapper valve or a trumpet valve inside that opens to allow an endpscope, laparoscope, or other instrument to pass through, and the valve closes when the laparoscope is removed. Some trocar/cannula devices also contain a duckbill valve to assist in sealing the trocar. The cannulas are typically about 6 inches or 15 centimeters long, and come in diameters matching various laparoscopic devices, generally from 2 to 15 mm.

Some surgeons use bare cannulas, secured only by a tight fit with the skin and fascia. However, cannulas frequently slip out of the body during use, disrupting the procedure and possibly endangering the patient. To prevent this danger, surgeons have devised a variety of methods to secure the cannula to the body and prevent it from slipping out of the body. Some cannulas are provided with threaded sleeves fixed to the cannula. Some cannulas are provided with a threaded gripper with a smooth inner bore that matches the size of the cannula, so that the cannula can slide inside the gripper as shown in FIG. 2. The gripper stabilizes the cannula so that it will not slip out of the body inadvertently, but can be easily slipped out when the surgeon wants. The threaded gripper is simply screwed into the incision in the skin. This option permits the ready insertion and removal of smooth walled cannulas by sliding them in and out of the gripper. Other grippers have been used, such as the gripper with expandable arms, the gripper with inflatable balloon on the outside, and the Hasson cannula. These devices are illustrated in Oshinsky, et al., Laparoscopic Entry and Exit, reprinted in Urologic Laparoscopy at 91–101 (Das & Crawford ed. 1994). These devices are variously referred to as threaded skin seals, screw skin seals, skin anchors, obturators, grippers, trocar stabilizers, or cannula stabilizers.

The surgeon usually needs to place several trocars and cannulas into the abdomen and inserts as many as needed to accomplish the intended operation. The first cannula placed through the belly button is used to insert a laparoscope so that the placement of other trocars and cannulas can be viewed from inside the abdomen. After several cannulas are in place, the surgeon can view the procedure through any port and can insert laparoscopic scissors, cutters and graspers, and other tools through the cannulas in order to perform the surgery. The typical endoscopic graspers 3 used for stitching inside the abdomen are shown, deployed inside the cannulas, in FIG. 2. A bare cannula 4 is used with endoscopic graspers 3a. Another pair of laparoscopic graspers 3b is inserted into a cannula 4a that is inserted through a threaded gripper 5. A third cannula 6, shown with a threaded outer surface, is provided for an endoscope 34 that is inserted into the workspace to provide the surgeon with a video view of the graspers 3a and 3b and body tissue.

The arrangement of the cannulas and trocars is required because the abdomen must be inflated to make room for the surgeon to work. The small diameter of the cannulas keeps the incisions small, and the matching diameter of the laparoscopic instruments is necessary to prevent leakage of the insufflation gas from the abdomen. Laparoscopic instruments of various designs are available, and they generally are about 5 to 12 mm in diameter (to match the inside bore of the cannulas) and about 10 to 40 cm in length. They are long and therefore difficult to use, and they are usually used when the surgeon can see them only through the laparoscope. Modern laparoscopic procedures require the surgeon to view the procedure on a video monitor. It may take a surgeon a lot of practice before becoming comfortable and skillful with the laparoscopic graspers, grippers, and scissors. These tools are more difficult to use than the surgical tools that every surgeon uses in normal surgery, such as those shown in FIG. 3, in use during open laparotomy. The normal graspers are shown in use while the surgeon is tying off a suture. This normal procedure is familiar to a large number of surgeons. The normal surgical graspers 7a and 7b are shown in use in FIG. 3, suturing body tissue 8 with suture 9, and it can readily be appreciated that the laparoscopic graspers shown in FIG. 2 require significantly more skill than the normal surgical tools. One of the drawbacks of the known cannulas and grippers is that they are adapted to admit only relatively narrow instruments, and are therefore generally unsuited for use with ordinary open incision surgical tools.

It would be advantageous to use normal surgical tools during laparoscopic procedures, but this is usually not permitted by the typical construction of the trocars and cannulas that are too narrow, long, and rigid to permit passage of the normal surgical tools. Most surgeons are very well trained in using conventional nonendoscopic instruments, such as the open incision graspers shown in FIG. 3, and numerous procedures involving the graspers such as tying off a suture are well known and well practiced. The endoscopic instruments shown in FIG. 2, on the other hand, are not well known and well practiced, and generally require significantly more skill than the more familiar open incision instruments. Thus, there is a need to provide cannulas and grippers that would accommodate the instruments used in open incision procedures.

SUMMARY OF THE INVENTION

In a typical endoscopic or laparoscopic operation, a surgeon creates a working space inside the body through insufflation. To create the working space for abdominal surgery, the surgeon makes a small incision at, for example, the inferior margin of the umbilicus 1 as shown in FIG. 1, and then uses his fingers or a dissecting tool, such as a blunt nosed obturator, to prepare a point of injection. The surgeon then inserts a Verres needle 2 into the abdominal cavity, and causes a pressurized gas such as $CO_2$ to flow through the needle and into the abdominal cavity. This inflates the abdomen, as shown in FIG. 1, and provides a working space for the surgeon. The needle may then be removed, and a cannula or trocar/cannula combination may be inserted into the incision. Additional incisions may also be made, and the first incision may be used to insert a laparoscope to assist in the placement of the other incisions. The additional incisions may each receive a cannula and, once several cannulas are in place, the surgeon can view the procedure and/or insert laparoscopic scissors, cutters, graspers, or other tools through any of the cannulas.

As mentioned above, the trocars and cannulas can be used in endoscopic blood vessel surgery, laparoscopic cholecystectomy, and laparoscopic hernia repairs where a workspace is created under the skin. In the blood vessel harvesting operation where the saphenous vein is to be removed, a surgeon creates a tunnel between two small incisions over the saphenous vein. Then a cannula and skin seal are inserted into each incision. The tunnel is insufflated through one of the cannulas. In these procedures, the laparoscopic instruments are also inserted into the working space through the cannulas, and the surgeon can watch the surgery through a laparoscope inserted through one of the cannulas.

The devices presented herein allow for use of normal surgical tools (such as the forceps and scissors used in open incision surgery) in laparoscopic procedures. The skin seal is fitted with one or more balloons on the inner bore. These balloons can be inflated after the skin seal is inserted into the incision into the abdomen Placement of the skin seal can be accomplished as usual, with the aid of a blunt or sharp trocar or cannula placed within the threaded skin seal. The threaded skin seal can be made of rigid plastic, as is customary, or preferably it may be made of soft and pliable material such as latex or silicone rubber. When the threaded skin seal is in place, the trocar may be removed and the balloon may be inflated until it expands to fill the inner bore of the threaded skin seal, thus sealing the bore to maintain the pressure created inside the abdomen with the insufflation gas. The balloons are soft and pliable and can conform around the elements of the instruments as they are moved about during use. Thus, normal or conventional surgical instruments may be passed between the balloons. Both normal surgical instruments and laparoscopic instruments may be inserted into the body through the balloons without disrupting the seal created by the balloons. The balloon is soft and pliable so that normal surgical tools may be operated inside the inflated balloon segments, and the balloon segments will not hamper the operation of the tool to a significant degree. The skin seal may be provided with a balloon membrane that expands outside the lumen of the skin seal to create a dumbbell, dog bone, or bowtie shaped balloon which pinches the skin and, when necessary, fills the lumen of the skin seal.

More than one tool may be inserted through a single skin seal because the balloons are sufficiently pliable and may be inflated to a lesser degree. In this manner, normal surgical instruments may be used in laparoscopic procedures, taking advantage of the fact that they are easier to use and more surgeons know how to use them, compared to the long laparoscopic instruments. The balloon filled skin seal may be used also as a seal for laparoscopic incisions which are no longer necessary or which the surgeon desires to plug temporarily while still leaving a skin seal in place for later use.

DETAILED DESCRIPTION OF THE DRAWINGS

The cannulas and grippers described below allow for use of normal surgical instruments in laparoscopic surgical procedures. The typical gripper configuration is modified by adding a balloon or inflatable membrane to the inner bore of the gripper and adding an inflation port to the wall of the gripper to allow for inflation of the balloon. When the balloon is inflated, it closes off the inner bore of the gripper so that it provides an airtight seal during insufflation. The balloon is pliable so that tools can be inserted through the inner bore of the balloon, and the balloon expands around the surgical tool to maintain the seal with little or no leakage of insufflation gas.

Figure 4:
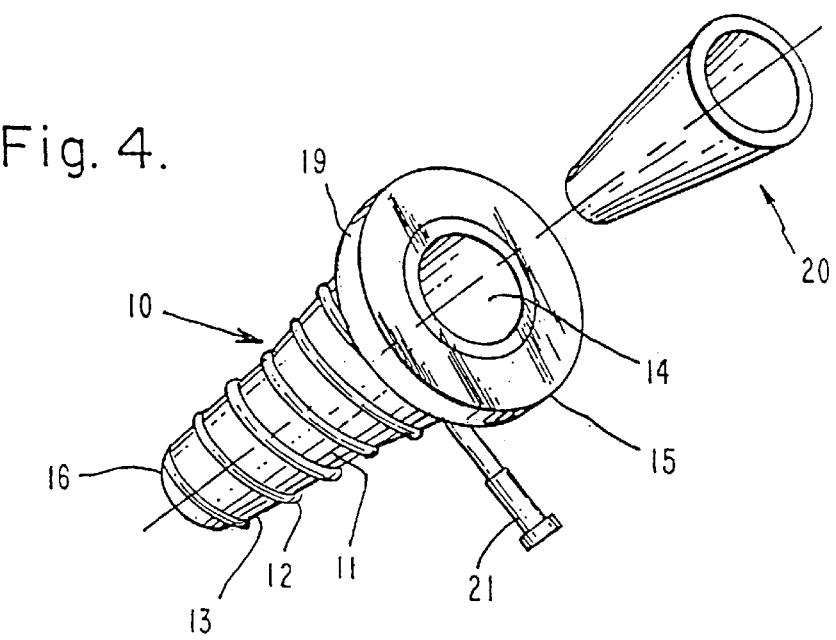
FIG. 4 is an exploded view of a cannula with an inflatable balloon inside.

Referring to FIG. 4, the threaded skin seal 10 is made of a funnel or tube 11 with a generally conical or frustum outer shape with screw threads 12 provided on the outer surface 13. The inner bore 14 is conical or funnel shaped, conforming generally to the shape of the outer shape. Overall, the skin seal is funnel shaped, and the proximal end 15 of the threaded skin seal has a large opening, and the distal or bottom end 16 has a smaller opening. The distal or bottom portion 16 of the threaded skin seal may have a straight or cylindrical bore to provide a tight fit with cannulas that have an outer diameter matching the inner diameter of this straight bore. The distal or bottom portion of the skin seal may have a straight or cylindrical outer shape to make it easier to screw the skin seal into an incision, and this straight section may be made of variable length to match the different thickness of fat which will be encountered in different patients. The proximal end preferably has a conical inner bore to facilitate insertion of tools into the opening and through the cannula, but the inner bore may be straight. The proximal end may also be described as flared and may be gradually flared in relation to the distal end, as though trumpet shaped, or flared in discrete fashion as in a typical funnel, with a straight tube at distal end and a conical segment at the proximal end. The screw threads constitute a fastening means, and may be replaced with other fastening means such as a circumferentially ribbed outer contour or a longitudinally grooved outer contour. As shown, a flange 19 may be provided on the proximal end of the cannula for ease in handling. The flange 19 also provides a convenient means for mounting the bellows onto the cannula. The skin seal is preferably 1 to 3 inches or about 2 to 8 centimeters long.

A balloon membrane 20 has a generally conical or frustum shape matching the inner bore of the threaded skin seal and having the same overall length of the threaded skin seal. The balloon membrane fits inside the threaded skin seal and is sealed to the skin seal funnel at the upper edge and lower edge of the balloon membrane. The balloon membrane may be shorter than the skin seal, and may be sealed to the inner surface of the skin seal at points inside the skin seal, rather than at the immediate distal and proximal edges of the skin seal. Also, the balloon membrane may be longer than the skin seal and may be cuffed or folded back around the outside of the skin seal at the proximal and distal ends and sealed at the cuffs.

An inflation port 21 is provided comprising a hole in the wall 22 of the threaded skin seal. An inflation tube 23 or Luer fitting connects the inflation port to a suitable pump such as the syringe 24 shown in FIG. 5 or the squeeze pump 25 shown in FIG. 6. Where the syringe is used, the membrane may be inflated and deflated repeatedly by pushing and pulling on the syringe plunger 26, thus forcing air into the bladder and sucking air out of the bladder. A one-way valve or stopcock may be used to seal the membrane so that the pump or syringe may be detached from the skin seal for more convenient use. Alternately, an inflation port can be provided at the distal tip of the skin seal, comprising an open airway between the inflatable membrane and the insufflated workspace. In this manner, the insufflation gas enters the skin seal from inside the body to pressurize and inflate the inflatable membrane. In this manner, an automatic seal is created upon insertion of the skin seal into the insufflated space. This simplifies placement and use of the skin seal because there is no need for a separate syringe or pump to inflate the membrane.

In the preferred embodiment, the bladder 20 is made of biocompatible elastomeric or elastic material, such as latex, silicone rubber, or any other suitable compliant material, elastic material, or inflatable material. The cannula 10 is made of rigid or flexible material, soft or hard plastic, high density or low density polyethylene, polypropylene, thick latex, silicone rubber, or any other suitable material including plastic, elastic, or nonelastic biocompatable material.

Figure 5:
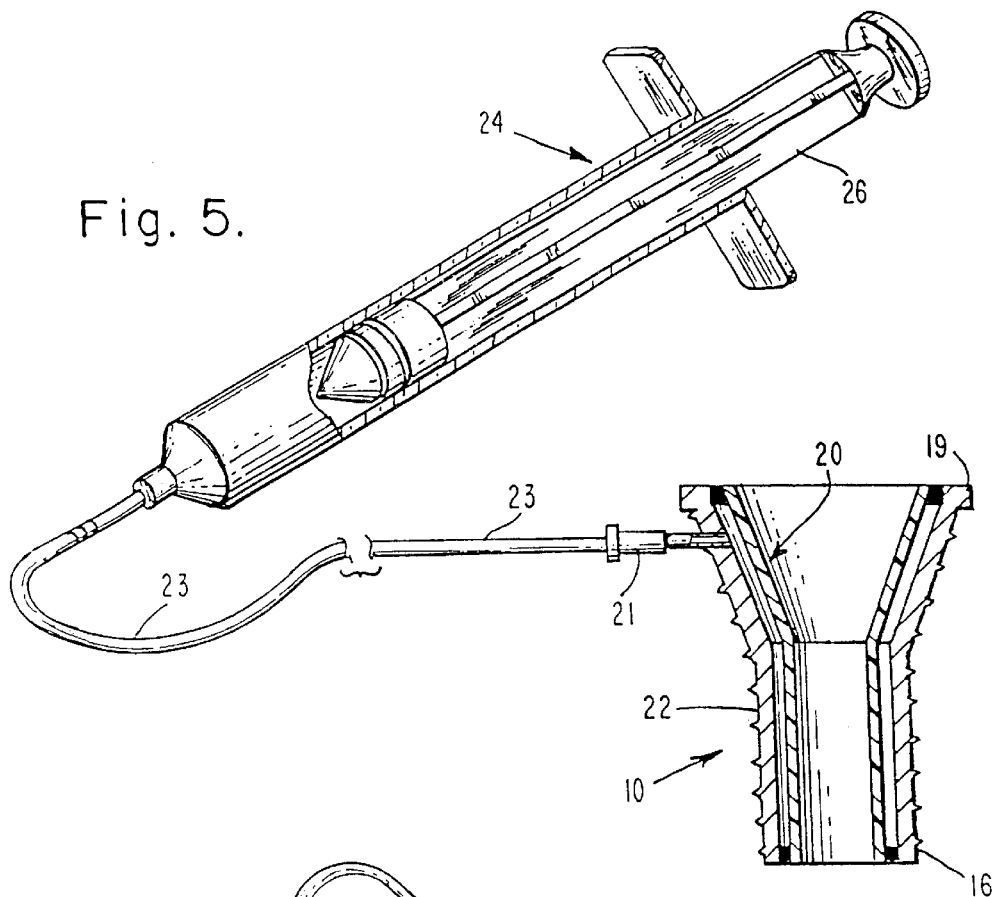
FIG. 5 is a cross sectional view of the cannula with the inflatable balloon inside.

As shown in FIGS. 4 and 5, the inflatable skin seal may be constructed by applying an elastic cylindrical or conical balloon membrane 20 to the inner bore of skin seal cannula 10 and sealing the distal end of the balloon to the distal end of the cannula and sealing the proximal end of the balloon to the proximal end of the cannula, thereby creating an inflatable space between the cannula and the membrane. Alternatively, a fully formed balloon bladder, comprising an inner and outer conical membranes sealed to each other at their distal and proximal ends can be provided and fixed to the inner bore of the cannula. The overall shape of the balloon will be conical, funnel shaped, or flared to match the shape of the inside of the skin seal. While one balloon is depicted in each of the figures, two or more balloons may be used to guard against the possibility of rupture and loss of insufflation pressure during an operation, or to facilitate manufacture, or to facilitate use of the skin seal with particular tools. A membrane seal may provided at any cross sectional plane, within the skin seal, to guard against loss of insufflation pressure.

Figure 6:
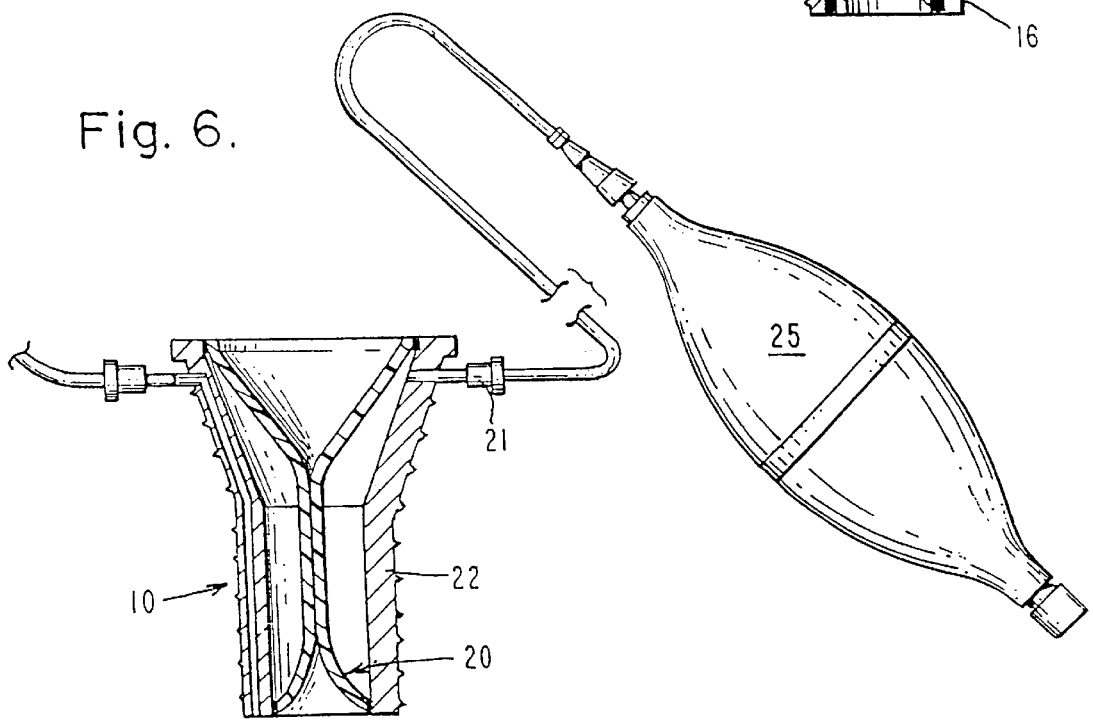
FIGS. 6, 6a and 6b show cross sectional views of the cannula with the inflatable balloon shown in its inflated state.
Figure 6A:
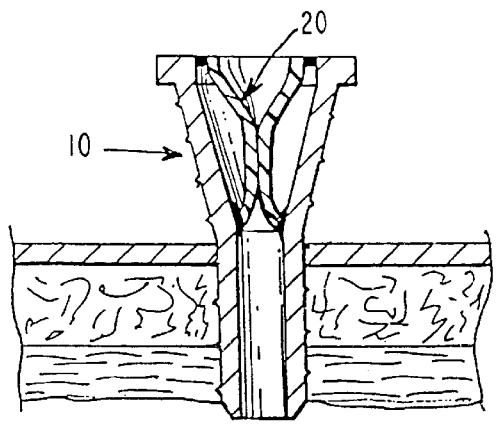
Figure 6B:
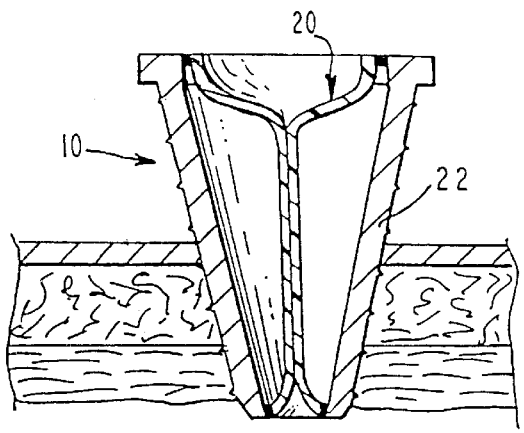

FIG. 6 shows the inflatable skin seal with the membrane in its inflated condition. The squeeze pump 25 is used to force air in the space between the bladder 20 and the wall of the cannula, causing the membrane to inflate within the cannula. The inflated membrane can be inflated until it completely obstructs the inner bore of the cannula and provides an airtight seal between the distal and proximal ends of the cannula. The cannula can be thin-walled and flexible enough to expand, as well, thereby further improving the seal between the cannula and the skin incision. As shown in FIG. 6a, the membrane need not extend for the full length of the cannula, but may instead be sealed to the inner bore at various points inside the cannula. The cannula in FIG. 6a has a balloon 20 only in the conical inner bore of the proximal section of the cannula, and this facilitates use of graspers, scissors, and other such instruments which might pinch the balloon when operated, or unnecessarily reduce the internal diameter of the narrowest portion of the cannula. As shown in FIG. 6b, the wall of the cannula may be made flexible enough to expand outward when the skin seal is inflated, so that any gaps or looseness in the seal between the outside of the skin seal, and the skin incision are closed by the expansion of the outer wall 22 of the skin seal.

Figure 7:
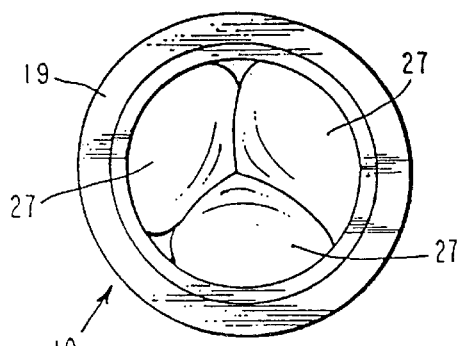
FIGS. 7 through 7c show end views, from the proximal end, of the cannula with inflatable balloon inside.

FIG. 7 shows the view of the inflated membrane viewed from the proximal end of the cannula. The membrane naturally bulges in two or more radial sections or segments 27 to fill the lumen of the cannula. The expansion of the balloon sections need not be controlled, but may be controlled to facilitate operation of graspers or other hinged and pinching tools. For example, the application of restrictors comprised of thickened strips along the length of the membrane, shown in FIG. 7a, may be applied to the membrane to inhibit expansion along the strip. Wire bands, plastic bands, or a line of adhesive gluing the balloon membrane to the skin seal may also be used to prevent expansion of the membrane along a longitudinal line of the membrane extending from the proximal end (or near the proximal end) to the distal end (or near the distal end) of the funnel. In this manner, a uniform expansion can be obtained with the membrane expanding from the walls of cannula to meet along a uniform plane. A pinching tool used in the cannula can be opened and closed along the plane defined by the inflated balloons, and the balloon will pliantly close upon the lumen, but allow the pinching tool to open and close with less chance of pinching and cutting the balloon. As shown in FIG. 7b, the inflatable membrane 20 may be placed on the inner bore of the skin seal in an eccentric manner, covering only a portion of the inner wall of the skin seal. FIG. 7c shows the eccentric inflatable membrane in its inflated state.

Figure 8:
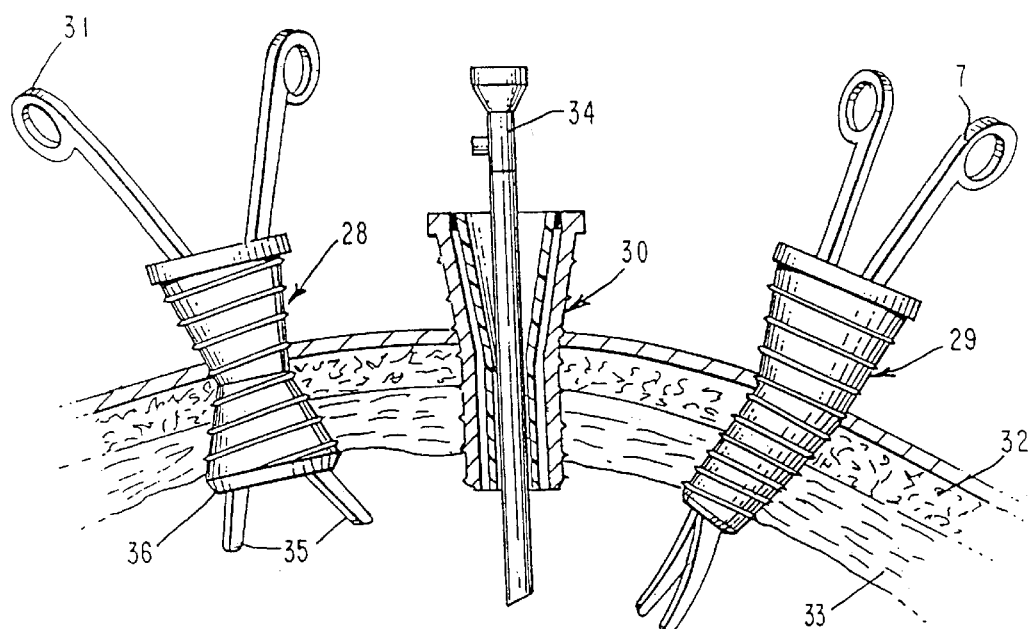
FIGS. 8 shows a pair of skin seals with the balloons inside, with normal surgical instrument inserted through the balloons, deployed in the manner of intended use.

FIG. 8 shows the skin seals 28, 29, and 30 with the balloon membranes inflated. Skin seal 28 has the funnel shape described above. A pair of normal surgical scissors, such as Metzenbaum scissors 31, is inserted through one skin seal 28 and a pair of normal surgical graspers 7 (examples include Kelly clamps, Kelly placenta forceps, and Mayo clamps) is inserted through the skin seal cannula 29 to perform operations beyond the distal tip of the cannula. The skin seals are shown screwed into incisions through skin 32 and subcutaneous fat 33, and they may also extend through the peritoneum or other tissue when appropriate to the operation. An endoscope or laparoscope 34 which can be inserted through one skin seal to provide a view of the procedure is shown in the central skin seal 30. Because the balloon is pliable and conforms around any device within the skin seal, the graspers may be manipulated inside the cannula without breaking the insufflation seal. As the graspers 7 are manipulated, the membrane conforms around graspers, but yields to allow the graspers to be opened, closed, twisted, pushed, and pulled within the skin seal without substantially degrading the seal created by the membrane. It should be noted that a perfectly airtight seal is not necessary, and some leakage of insufflation gas or fluid is acceptable, so long as insufflation gas or fluid can be injected at a rate sufficient to make up for any loses. Where the cannula itself is made of a soft pliant material such as latex rubber or silicone rubber, the forceps may be manipulated even further, and deformation of the skin seal 28 will permit a wider range of motion for the forceps. Skin seal 28 is shown with a pair of conventional surgical scissors 31 or shears disposed through the skin seal. The scissors may be opened wide, as shown, and the distal or proximal end of the skin seal will yield and flare out to allow operation of the scissors through their full range of motion and opened through the full throw (the "throw" referring to the length of arc 35 over which the graspers or scissors may be opened) of scissors 31 or graspers, as illustrated by flared distal portion 36 of skin seal 28.

Figure 1:
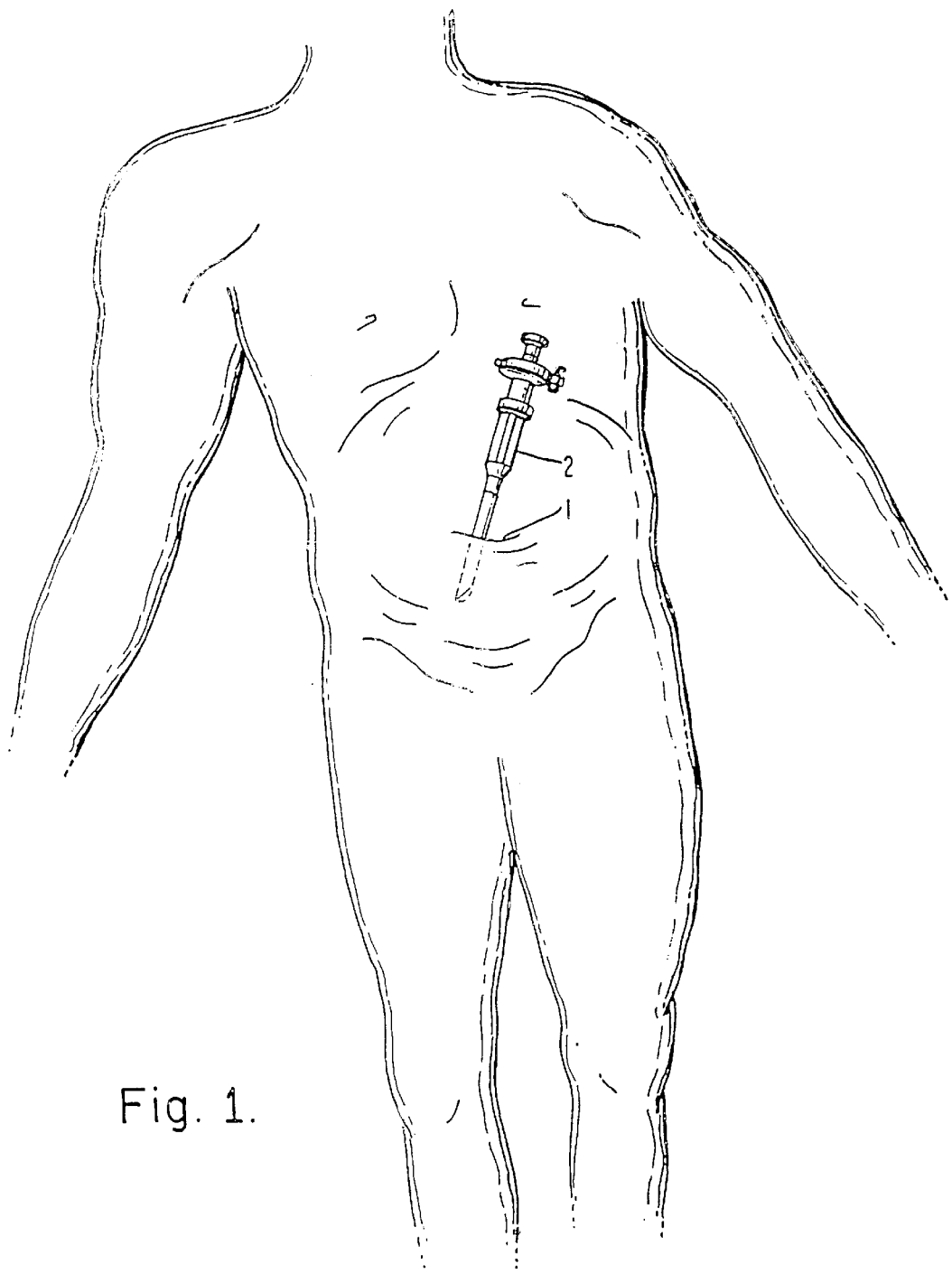
FIG. 1 is an external view of the abdomen of a patient undergoing insufflation.
Figure 2:
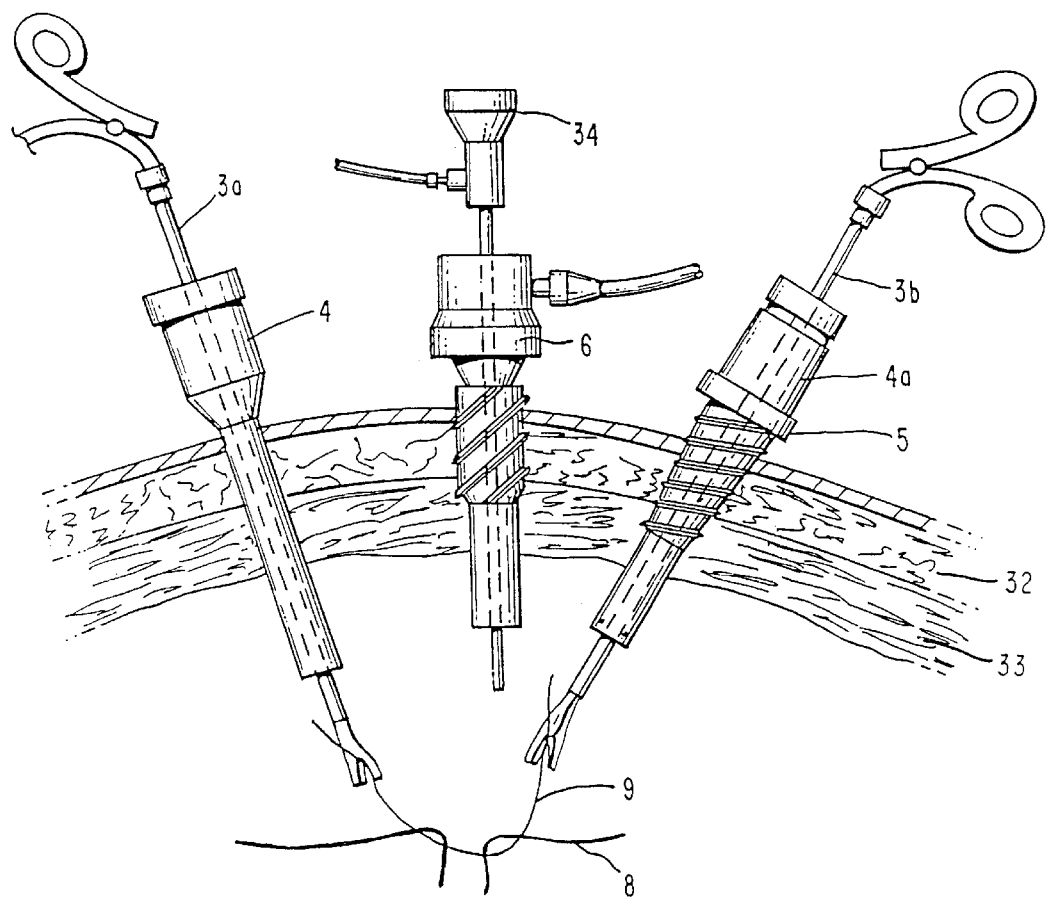
FIG. 2 is a cross section drawing of the insufflated abdomen of a patient with several trocars, cannulas and laparoscopic instruments in place for a laparoscopic procedure.
Figure 3:
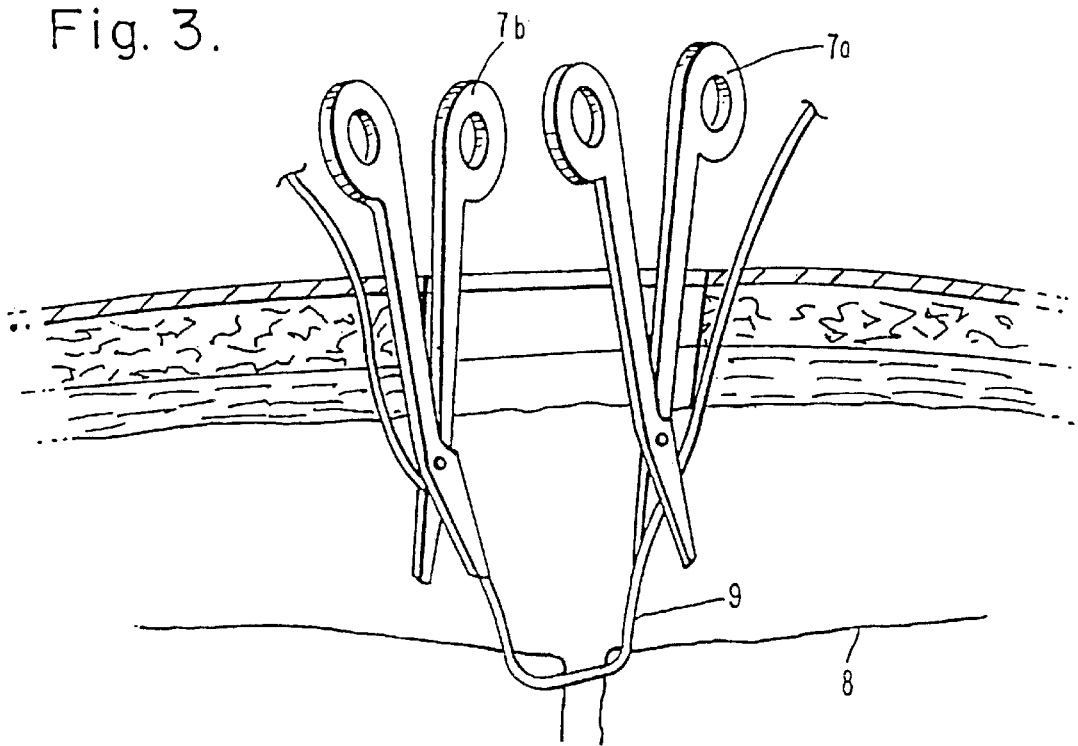
FIG. 3 is a view of an open laparotomy procedure using normal surgical forceps.

It will be readily appreciated that such operation would not be possible using standard cannulas. The normal surgical tools are much easier to use than the long laparoscopic instruments shown in FIG. 2. Also, the tools can be much larger and have much larger operating implements. For example, the cutting edges of scissors 31 are much longer that cutting edges on laparoscopic scissors and can cut much more quickly. A common method of dissecting tissue with normal scissors is to pierce connective tissue with the closed scissors and open the scissors, operating the scissors in backwards fashion, so that the dull outer edges of the scissors pull connective tissue apart. This can be done very quickly using the skin seals 29 and 30, as compared to slow and tedious snipping required when using long laparoscopic instruments.

Figure 9:
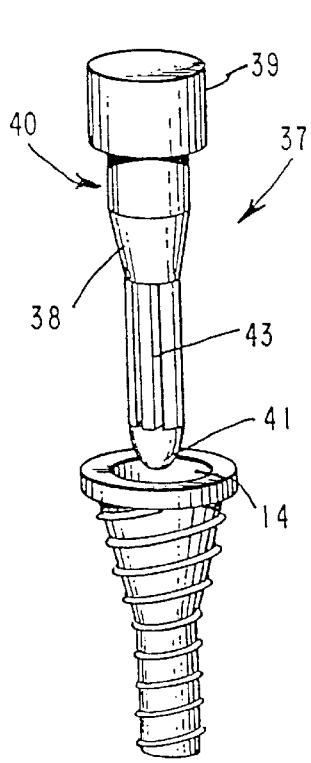
FIG. 9 shows a blunt obturator suited for use with the skin seal.
Figure 10:
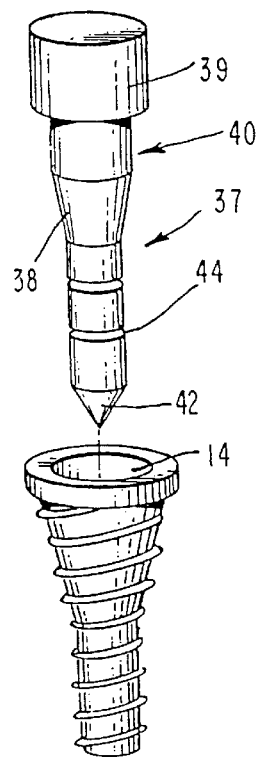
FIG. 10 shows a sharp trocar type obturator suited for use with the skin seal.
Figure 11:
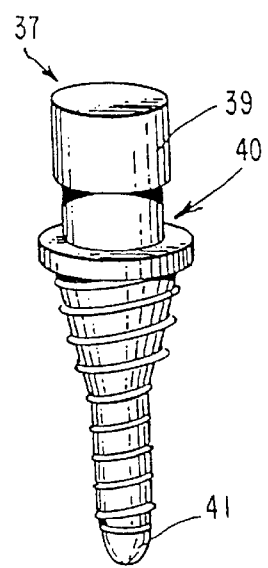
FIG. 11 shows the blunt obturator inserted in the skin seal.

Placement of the skin seals may be facilitated with special blunt obturators shown in FIGS. 9, 10, and 11. The blunt obturator 37 provides support for the skin seal as it is pushed and screwed into the incision. The blunt obturator comprises a peg 38 with an outer contour which matches the inner bore of the skin seal, a handle 39, a finger gap 40, and a blunt tip 41. The tip may be blunt and rounded, or it may be sharp and pointed, as illustrated by the sharp pointed trocar type tip 42 in FIG. 10, in which case the sharp point 42 can puncture body tissue. The obturator is placed inside the skin seal as shown in FIG. 11, and the assembly is screwed into the body as a unit. After the skin seal is in place, the obturator is removed to allow insertion of other devices into the skin seal. The finger gap 40 leaves some space for the surgeon to push against the flange of the skin seal while pulling the handle 39, thus avoiding the possibility that the skin seal will be pulled out of the body with the obturator 37. Because the obturator fits tightly inside the skin seal to give it support during insertion, it may inadvertently become sealed to the inside of the skin seal, especially if there is any leakage of body fluids or water into the skin seal. Any excessive force required to pull out the obturator could result in pulling the screw skin seal out of the skin incision. To prevent the need for such excessive force, the portion of the obturator which fits inside the skin seal may be provided with vacuum breakers in the form of scored lines or channels 43, circumferential grooves 44, or a roughened surface to prevent a vacuum from forming between the skin seal inflatable membrane. The scoring or roughening may take any form.

Figure 12:
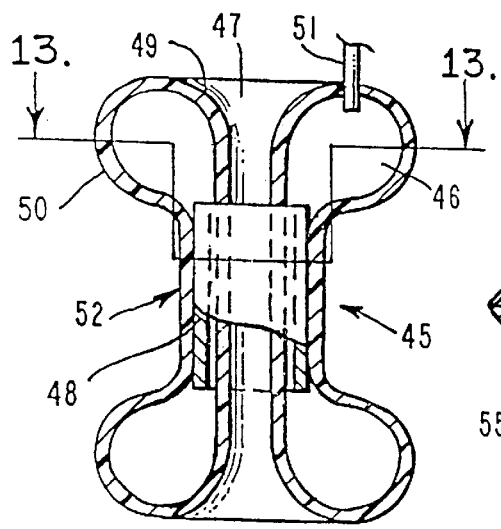
FIG. 12 shows a skin seal with balloons that expand outside the lumen of the skin seal.

FIG. 12 shows another embodiment of the skin seal in which the balloon is enlarged so that it expands outside the lumen of the skin seal. The skin seal 45 shown in FIG. 12 includes a dumbbell shaped balloon 46. The shape of the balloon may variously be described dog bone, bowtie, dumbbell, or butterfly shaped. The balloon 46 has a lumen 47 extending through the balloon and can be provided with a rigid cannula segment or stiffener tube 48 disposed within the balloon. The stiffener tube need only be stiff enough to provide support for the balloon during placement, so it is stiff in relation to the balloon membrane, but may, in fact, be very flexible and can be made of any plastic or elastic material or other materials suitable for the inflatable membrane.

The balloon may be formed by sealing together an inner balloon tube 49 and an outer balloon membrane 50. An inflation port 51 is provided on the outer dumbbell portion, but may also be provided on the waist portion 52 or even the inner dumbbell. When used during insufflation, an inflation port may be provided on the inner dumbbell in form of a simple airway provided in the inner dumbbell that allows insufflation gas to enter the balloon from the insufflated space. In this manner, the need for a separate source of inflation gas or fluid is avoided.

Figure 13:
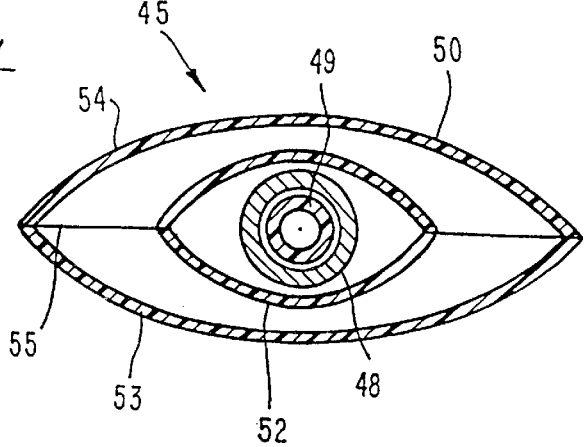
FIG. 13 shows a cross section of the skin seal with outer balloon.
Figure 15:
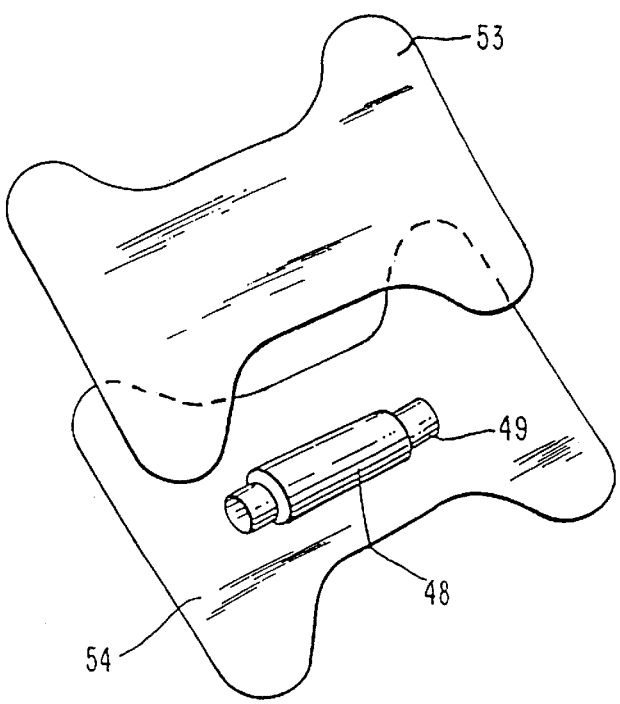
FIG. 15 shows an exploded view of the skin seal with outer balloons

The outer balloon membrane may be made of two or more pieces to create any desired outer shape. As shown in FIG. 13, the outer balloon membrane has an oval outer shape when inflated. The balloon may be provided with any other useful shape and may be round or toroidal, or oval, as shown. The balloon is formed of two pieces 53 and 54 that are heat sealed or sealed with adhesive along the seam 55. FIG. 13 also illustrates that the inner balloon tube 49 fits inside the lumen of the stiffener tube 48 while the outer balloon surrounds the stiffener tube. FIG. 15 shows an exploded view of the device with butterfly shaped balloon membranes 53 and 54, the tubular balloon membrane 47 extending across the "wingspan" or major length of the butterfly shaped membrane, and the stiffener tube 48 surrounding the tubular balloon membrane 47. With the tubular balloon membrane and the stiffener tube sandwiched between the butterfly shaped balloon membranes, the edges of the butterfly shaped membranes are sealed together, and the ends of the tubular balloon membrane are sealed to the edge of the butterfly shaped membranes at the middle of the outer edge of the wings, thereby forming a single balloon with an overall butterfly shape and a through hole extending across the wingspan. The balloon can be made of any suitable material, including polyethylenes, polyamide, polyurethanes, latex, or silicone rubber. The balloon may be elastic or nonelastic. The various pieces may be made of different material, for example the inner balloon tube may be made of an elastic material, and the outer balloon membranes may be made of nonelastic material.

The stiffener tube 48 may be a straight length of tube or it may be funnel shaped like the screw skin seals described above. The stiffener tube provides columnar support for the device so that it can be pushed through an incision in the skin. The stiffener tube may be made of any suitable material, including any material previously mentioned above and any material previously used for cannulas and trocars. The length of the stiffener tube is chosen to approximate the thickness of the skin and fat layers 32 and 27, and is preferably slightly shorter than the thickness of the skin and fat layer. The stiffener tube may be disposed inside the balloon pieces without being sealed in any way to the balloon pieces, or it may be sealed to either the inner or outer balloon pieces.

Figure 7A:
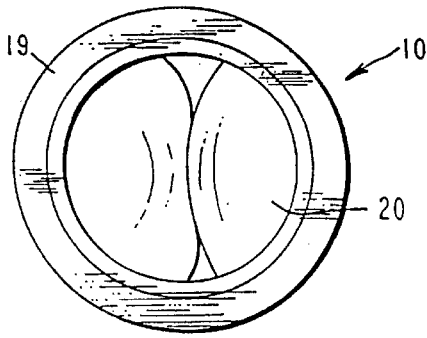
Figure 7B:
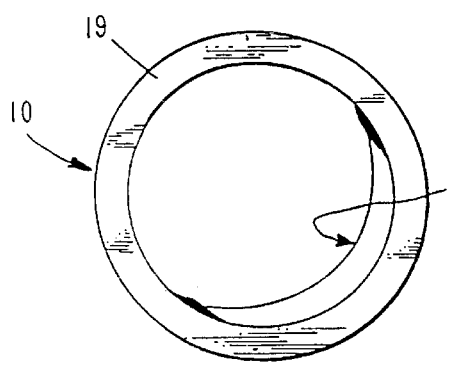
Figure 7C:
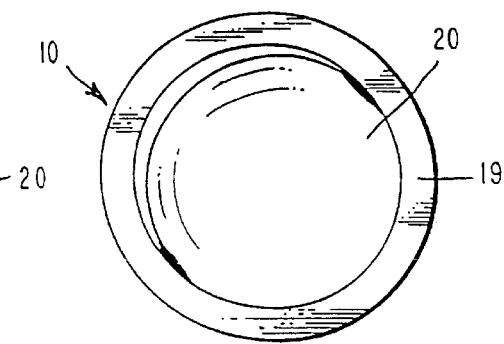
Figure 14:
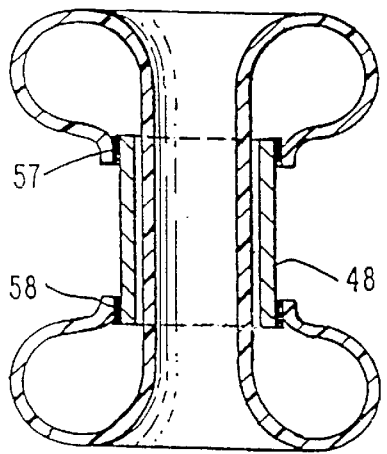
FIG. 14 shows an alternate embodiment of a skin seal with balloons which expand outside the lumen of the skin seal.

The inner balloon tube may be sealed along a circumference of the tube just as the balloon membrane of FIGS. 5 and 6 is sealed to the threaded skin seal, and it may be sealed to the stiffener tube along one or more longitudinal lines as shown in FIG. 7a. The inner balloon may also be provided with thickened longitudinal portions, metal, or plastic bands, etc., as described in reference to FIG. 7a to control inflation and encourage inflation toward a uniform plane in the center of the lumen. Also, the inner balloon 49 may be sealed to the stiffener tube 48 at both ends of the stiffener tube, as is the balloon membrane of the threaded skin seal, and inflated through an optional airway 56. The outer balloon pieces may be sealed to the outside of the stiffener tube, either by sealing the entire waist portion to the stiffener tube, or by dispensing with the waist portion and sealing the dumbbell portion of the balloons to the ends 57 and 58 of the stiffener tube, as shown in FIG. 14.

Figure 16:
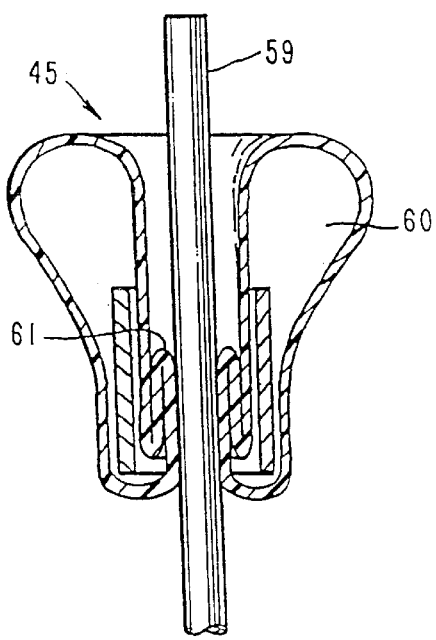
FIG. 16 shows the skin seal with outer balloon prepared for insertion into a skin incision.
Figure 17:
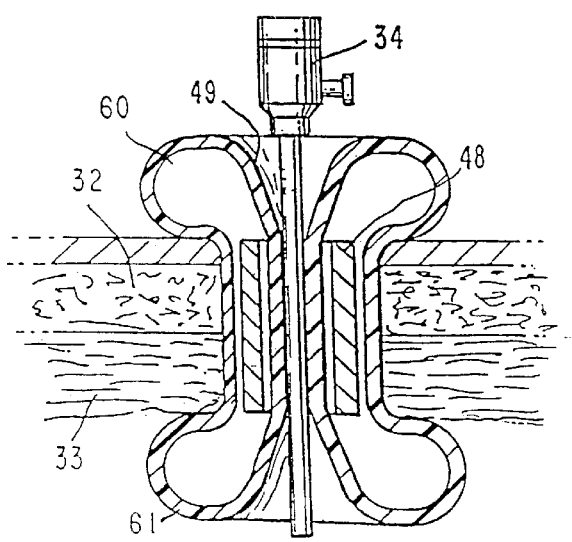
FIGS. 17 through 17b show the skin seal with outer balloon inserted into a skin incision.
Figure 17B:
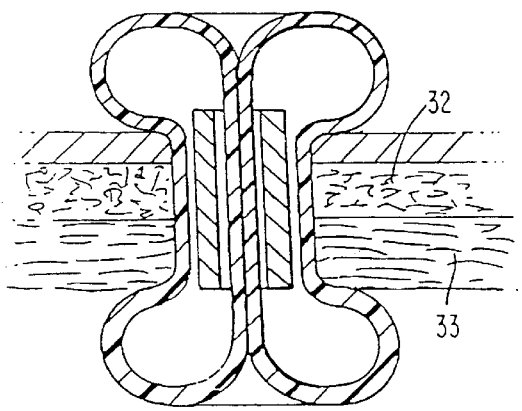
Figure 17A:
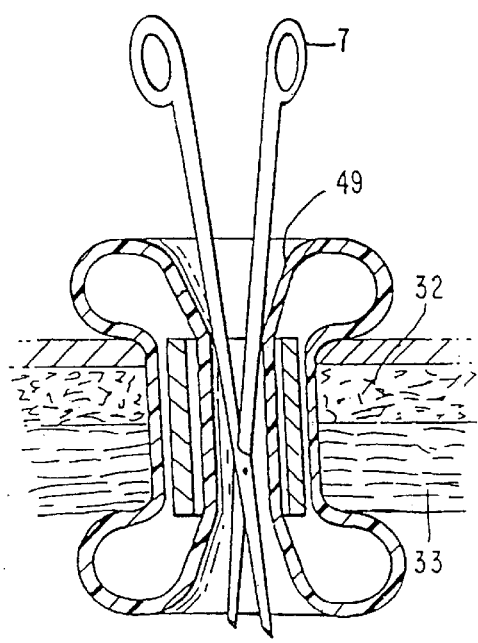

In use, the distal end of the deflated balloon is tucked into or pulled into the stiffener tube, as shown in FIG. 16. An obturator, trocar, or cannula 59 is placed inside the stiffener tube 48 to facilitate insertion of the skin seal into an incision. The cannula 59 is pushed into the incision along with the skin seal that rides over the cannula. With the cannula 59 in the incision, the skin seal 45 can be pushed over the cannula and into the incision. After the skin seal has been inserted into the incision, the cannula may be removed leaving the skin seal in place. Then the balloon can be inflated, as shown in FIG. 17. When the balloon is inflated, as shown in FIG. 17, the outer dumbbell portion 60 is inflated while the inner dumbbell portion 61 expands out of the stiffener tube and into the body and inflates to re-establish the dumbbell shape. When the balloon is inflated further, the expanding dumbbells clamp down on skin 32, fat 33, and other tissue trapped between the inner balloon portion 61 and outer balloon portions 60. The stiffener tube 48 prevents the inner balloon tube from collapsing at the waist 52, but the inner balloon may expand to fill the lumen or through hole 47. The inner balloon tube 49, when inflated to fill the through hole, acts as a seal for any device such as the endoscope 34 placed through the lumen, as shown in FIG. 17. A trocar or cannula may be inserted into the body through the lumen of the skin seal to allow inserting of laparoscopic instruments through the cannula or laparoscopic instruments, and normal surgical instruments may be inserted through the skin seal, as shown in FIGS. 17a and 17b, where the inner balloon tube expands to conform around the instruments. FIG. 17a shows the same skin seal with a pair of normal graspers used for open surgery inserted into the body through the skin seal. FIG. 17b shows the skin seal inflated so that the inner balloon tube 49 completely fills the lumen of the skin seal, thus maintaining the insufflation of the working space below the skin seal.

Figure 18:
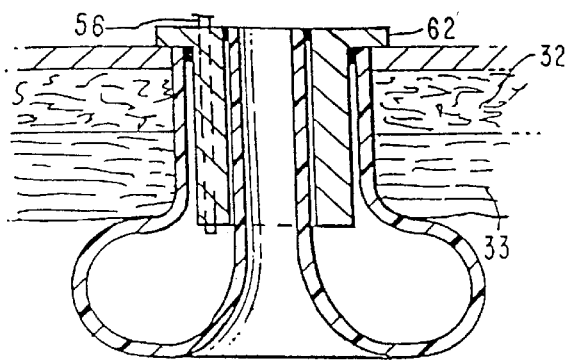
FIG. 18 shows an alternate embodiment of the skin seal.

In another embodiment, only the inside or distal end of the balloon expands outside the skin seal. As shown in FIG. 18, the stiffener tube is provided with a flange 62 on the proximal end. The inner balloon tube is sealed to the inside of the stiffener tube at the proximal end of the tube. The outer balloon portion is sealed to the outside surface of the stiffener tube. The inner or distal dumbbell portion is expanded inside the body, and inflation of the distal dumbbell portion clamps the skin and fat between the flange and the distal balloon. When the central lumen is not occupied by an instrument, the balloon can be inflated so that the inner balloon tube expands into the central lumen and establishes a seal between the insufflated work space and the outside of the body. The seal can be supplied in a variety of sizes, with stiffener tubes of various sizes to match commercially available trocars, cannulas and laparoscopic instruments. The size of the balloon and the length of the stiffener tube can be varied to fit incisions of various sizes required by the many different operations with which the skin seal can be used. The skin seal may be used for laparoscopic access in any procedure, and can also be used to compress bleeding incisions and plug unneeded incisions during laparoscopic surgery.

The skin seals described above can be used for any endoscopic or laparoscopic surgery to permit use of normal surgical instruments, i.e., ordinary open incision surgical instruments. While the skin seals described above are useful in procedures requiring insufflation, they may also be used in other endoscopic or laparoscopic procedures. The use of the skin seal in any endoscopic or laparoscopic procedures will allow deployment of normal surgical tools while protecting the area of the incision from trauma caused by the operation of the surgical instruments. Where insufflation or flushing is required, the bladder in the skin seal may be inflated to prevent undesired flow out of the cannula. Also, although the skin seal described above has been described in the best known embodiments, fabricated with suitable materials to the inventors, the particular materials and shapes depicted in the illustrations may be altered and improved upon without departing from the inventions as claimed. It is specifically contemplated that the materials be improved upon. Furthermore, although the devices have been described in relationship to surgery requiring insufflation and endoscopic or laparoscopic surgery, the claimed devices and methods may be used in surgical and nonsurgical applications wherever the features of these device and methods prove beneficial.

What is claimed is:

1. A surgical access device comprising:
a flexible tube having a proximal end, a distal end and an inner bore, and a flange on said proximal end;
a balloon bladder inserted into the bore of the flexible tube, said balloon bladder comprising:
an inner membrane with a distal end and a proximal end;
an outer membrane with a distal end, a proximal end and an inflation opening; and
an inflation port communicating with said inflation opening on the outer membrane of the balloon bladder,
wherein the proximal end of the inner membrane is sealed to the proximal end of the outer membrane and the distal end of the inner membrane is sealed to the distal end of the outer membrane.

2. A surgical access device comprising:
a flexible tube having a proximal end, a distal end and an inner bore, and fastening means comprising protrusions on the outer surface of said flexible tube;
a balloon bladder inserted into the bore of the flexible tube, said balloon bladder comprising:
an inner membrane with a distal end and a proximal end;
an outer membrane with a distal end, a proximal end and an inflation opening; and
an inflation port communicating with said inflation opening on the outer membrane of the balloon bladder,
wherein the proximal end of the inner membrane is sealed to the proximal end of the outer membrane and the distal end of the inner membrane is sealed to the distal end of the outer membrane.

3. A surgical access device comprising:
a flexible tube having a proximal end, a distal end and an inner bore, and fastening means comprising screw threads on the outer surface of said flexible tube;
a balloon bladder inserted into the bore of the flexible tube, said balloon bladder comprising:
an inner membrane with a distal end and a proximal end;
an outer membrane with a distal end, a proximal end and an inflation opening; and
an inflation port communicating with said inflation opening on the outer membrane of the balloon bladder,
wherein the proximal end of the inner membrane is sealed to the proximal end of the outer membrane and the distal end of the inner membrane is sealed to the distal end of the outer membrane.

4. A surgical access device comprising:
a flexible tube having a proximal end, a distal end and an inner bore, and fastening means comprising circumferential ribs on the outer surface of said flexible tube;
a balloon bladder inserted into the bore of the flexible tube, said balloon bladder comprising:
an inner membrane with a distal end and a proximal end;
an outer membrane with a distal end, a proximal end and an inflation opening; and
an inflation port communicating with said inflation opening on the outer membrane of the balloon bladder,
wherein the proximal end of the inner membrane is sealed to the proximal end of the outer membrane and the distal end of the inner membrane is sealed to the distal end of the outer membrane.

5. A surgical access device comprising:
a flexible tube having a proximal end, a distal end and an inner bore, and fastening means comprising grooves on the outer surface of said flexible tube;
a balloon bladder inserted into the bore of the flexible tube, said balloon bladder comprising:
an inner membrane with a distal end and a proximal end;
an outer membrane with a distal end, a proximal end and an inflation opening; and
an inflation port communicating with said inflation opening on the outer membrane of the balloon bladder,
wherein the proximal end of the inner membrane is sealed to the proximal end of the outer membrane and the distal end of the inner membrane is sealed to the distal end of the outer membrane.

6. A surgical access device comprising:
a conical flexible tube having a proximal end, a distal end and an inner bore; and
a balloon bladder inserted into the bore of the flexible tube, said balloon bladder comprising:

an inner membrane with a distal end and a proximal end;

an outer membrane with a distal end, a proximal end and an inflation opening; and an inflation port communicating with said inflation opening on the outer membrane of the balloon bladder, wherein the proximal end of the inner membrane is sealed to the proximal end of the outer membrane and the distal end of the inner membrane is sealed to the distal end of the outer membrane.

7. The device of claim 6 wherein said balloon bladder is conical.

8. A surgical access device comprising:

a flexible tube having a proximal end, a distal end and an inner bore; and a balloon bladder inserted into the bore of the flexible tube, said balloon bladder comprising:

an inner membrane with a distal end and a proximal end;

an outer membrane with a distal end, a proximal end and an inflation opening; and an inflation port comprising a hole in the wall of the flexible tube communicating with said inflation opening on the outer membrane of the balloon bladder, wherein the proximal end of the inner membrane is sealed to the proximal end of the outer membrane and the distal end of the inner membrane is sealed to the distal end of the outer membrane.

9. A surgical access device comprising:

a flexible tube having a proximal end, a distal end and an inner bore, and a flange on said proximal end of said flexible tube;

an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

10. A surgical access device comprising:

a flexible tube having a proximal end, a distal end and an inner bore, and fastening means comprising protrusions on the outer surface of the flexible tube;

an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

11. A surgical access device comprising:

a flexible tube having a proximal end, a distal end and an inner bore, and fastening means comprising screw threads on the outer surface of the flexible tube; and an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

12. A surgical access device comprising:

a flexible tube having a proximal end, a distal end and an inner bore, and fastening means comprising circumferential ribs on the outer surface of the flexible tube; and an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

13. A surgical access device comprising:

a flexible tube having a proximal end, a distal end and an inner bore, and fastening means comprising grooves on the outer surface of the flexible tube; and an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

14. A surgical access device comprising:

a conical flexible tube having a proximal end, a distal end and an inner bore;

an expandable membrane having a proximal end, a distal end, and a lumen extending therethrough, the expandable membrane disposed coaxially within said inner bore of said flexible tube, wherein the proximal and distal ends of the expandable membrane are sealed to the flexible tube.

15. The device of claim 14 wherein said expandable membrane is conical.

16. A surgical access device comprising:

a flexible tube having a proximal end, a distal end and an inner bore;

an expandable membrane of a length less than the length of said flexible tube having a proximal end, a distal end, and a lumen extending therethrough, the expandable membrane disposed coaxially within said inner bore of said flexible tube, wherein the proximal and distal ends of the expandable membrane are sealed to the flexible tube.

17. The device of claim 16 wherein the proximal and distal ends of the expandable membrane are sealed to the bore of the flexible tube.

18. A surgical access device comprising:

a flexible tube having a proximal end, a distal end and an inner bore, and a flange on said proximal end of flexible tube;

an expandable membrane having edges, the expandable membrane disposed within said inner bore of said flexible tube, wherein the edges of the expandable membrane are sealed to the flexible tube; and an inflation port communicating with said expandable membrane.

19. A surgical access device comprising:

a flexible tube having a proximal end, a distal end and an inner bore, and fastening means comprising protrusions on the outer surface of the flexible tube;

an expandable membrane having edges, the expandable membrane disposed within said inner bore of said flexible tube, wherein the edges of the expandable membrane are sealed to the flexible tube; and an inflation port communicating with said expandable membrane.

20. A surgical access device comprising:

a flexible tube having a proximal end, a distal end and an inner bore and fastening means comprising screw threads on the outer surface of the flexible tube;

an expandable membrane having edges, the expandable membrane disposed within said inner bore of said flexible tube, wherein the edges of the expandable membrane are sealed to the flexible tube; and an inflation port communicating with said expandable membrane.

21. A surgical access device comprising:

a flexible tube having a proximal end, a distal end and an inner bore, and fastening means comprising circumferential grooves on the outer surface of the flexible tube;

an expandable membrane having edges, the expandable membrane disposed within said inner bore of said flexible tube, wherein the edges of the expandable membrane are sealed to the flexible tube; and an inflation port communicating with said expandable membrane.

22. A surgical access device comprising:

a flexible tube having a proximal end, a distal end and an inner bore and fastening means comprising grooves on the outer surface of the flexible tube;

an expandable membrane having edges, the expandable membrane disposed within said inner bore of said flexible tube, wherein the edges of the expandable membrane are sealed to the flexible tube; and an inflation port communicating with said expandable membrane.

23. A surgical access device comprising:

a conical flexible tube having a proximal end, a distal end and an inner bore;

an expandable membrane having edges, the expandable membrane disposed within said inner bore of said flexible tube, wherein the edges of the expandable membrane are sealed to the flexible tube; and an inflation port communicating with said expandable membrane.

24. A surgical access device comprising:

a flexible tube having a proximal end, a distal end and an inner bore;

an expandable membrane having edges, the expandable membrane disposed within said inner bore of said flexible tube, wherein the edges of the expandable membrane are sealed to the flexible tube; and an inflation port comprising a hole on the surface of the flexible tube communicating with said expandable membrane.

25. A surgical access device comprising:

a flexible tube having a proximal end, a distal end and an inner bore;

an expandable membrane having edges, the expandable membrane disposed within said inner bore of said flexible tube, wherein the edges of the expandable membrane are attached to the flexible tube to form a seal; and an inflation port comprising an opening in the seal between the expandable membrane and the flexible tube communicating with said expandable membrane.

* * * * *